United States Patent
Xu et al.

(10) Patent No.: US 11,834,387 B1
(45) Date of Patent: Dec. 5, 2023

(54) QUATERNARY AMMONIUM SALT AND PREPARATION METHOD AND USE THEREOF AS INHIBITOR, AND WATER-BASED DRILLING FLUID AND USE THEREOF

(71) Applicants: Yangtze University, Hubei (CN); Jingzhou Jiahua Technology Co., Ltd., Hubei (CN)

(72) Inventors: Mingbiao Xu, Jingzhou (CN); Fuchang You, Jingzhou (CN); Kai Jiao, Jingzhou (CN); Shusheng Zhou, Jingzhou (CN)

(73) Assignees: Yangtze University, Jingzhou (CN); Jingzhou Jiahua Technology Co., Ltd., Jingzhou (CN)

( * ) Notice: Subject to any disclaimer, the term of this patent is extended or adjusted under 35 U.S.C. 154(b) by 0 days.

(21) Appl. No.: 18/116,423

(22) Filed: Mar. 2, 2023

(30) Foreign Application Priority Data

Sep. 9, 2022 (CN) .......................... 202211101253.9

(51) Int. Cl.
*C07C 211/62* (2006.01)
*C07C 209/60* (2006.01)
*C07C 209/12* (2006.01)

(52) U.S. Cl.
CPC .......... *C07C 211/62* (2013.01); *C07C 209/12* (2013.01); *C07C 209/60* (2013.01)

(58) Field of Classification Search
None
See application file for complete search history.

(56) References Cited

U.S. PATENT DOCUMENTS

2015/0329487 A1* 11/2015 Schmitt .................... B01J 29/70
548/545

* cited by examiner

*Primary Examiner* — Sudhakar Katakam
*Assistant Examiner* — Jennifer C Sawyer
(74) *Attorney, Agent, or Firm* — Harness, Dickey & Pierce, P.L.C.

(57) ABSTRACT

Provided are a quaternary ammonium salt and a preparation method and use thereof as an inhibitor, and a water-based drilling fluid and use thereof. The quaternary ammonium salt has a structure shown in formula I, wherein, in the formula I, $R_1$ is selected from the group consisting of —H and —COOH; $R_2$ is selected from the group consisting of —H and —CH$_2$—COOH; $R_3$ is selected from the group consisting of —NH—CH$_2$—CH$_2$—CH$_2$—NH$_2$, —NH—CH$_2$—CH$_2$—NH$_2$, —NH—CH$_2$—CH$_2$—OH, —O—CH$_2$—CH$_2$—NH$_2$, —N—(CH$_2$—CH$_2$—OH)$_2$, and —O—CH$_2$—CH$_2$—NH—CH$_2$—CH$_2$—OH; and n and m are independently 10 to 15.

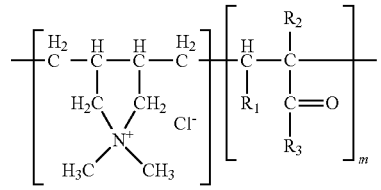

formula I

14 Claims, No Drawings

QUATERNARY AMMONIUM SALT AND PREPARATION METHOD AND USE THEREOF AS INHIBITOR, AND WATER-BASED DRILLING FLUID AND USE THEREOF

CROSS REFERENCE TO RELATED APPLICATION

This patent application claims the benefit and priority of Chinese Patent Application No. 202211101253.9 filed with the China National Intellectual Property Administration on Sep. 9, 2022, the disclosure of which is incorporated by reference herein in its entirety as part of the present application.

TECHNICAL FIELD

The present disclosure relates to the technical fields of petroleum drilling engineering and oilfield chemistry, and in particularly to a quaternary ammonium salt and a preparation method and use thereof as an inhibitor, and a water-based drilling fluid and use thereof.

BACKGROUND

With the continuous development and research of drilling exploitation technologies of unconventional oil and gas resources, tight gas has become an important field of the exploration and development of unconventional oil and gas resources in China, with great development potential. Tight gas reservoirs are complex and diverse, with strong heterogeneity, low porosity, low permeability, and micro-fractures; under the action of drilling fluid column pressure and capillary force, the filtrate is easy to invade the formation, causing the formation rock to hydrate and swells. Most of the overlying rocks on tight gas reservoirs are mainly soft mudstone, which is highly easy to hydration pulping. For the economic development of the tight gas reservoirs, a simplified wellbore structure is adopted to save investment, that is, one wellbore operation is adopted from the surface layer to the tight gas reservoir, which poses a great challenge to the water-based drilling fluid for tight gas to inhibit soft mudstone pulping as well as the wellbore stability and friction of long horizontal wells. At present, horizontal wells with a length of more than 3000 m are being constructed in China. Due to the large length of the horizontal section, there are many contact surfaces between drilling tools and the borehole wall, resulting in large friction and torque during the drilling, which is not conducive to drilling safety and efficiency.

In order to ensure the safety and efficiency of drilling, it is necessary to improve the inhibition, lubrication, and plugging performances of drilling fluid, and oil-based drilling fluids are generally used. However, the oil-based drilling fluids have problems such as high cost, difficult disposal of drilling cuttings, and environmental pollution; moreover, water-based drilling fluids are facing particularly prominent problems in terms of frictional torque, wellbore stability, and inhibition of pulping. Based on this, in order to solve the problems of mudstone hydration pulping, wellbore instability, and high friction in horizontal wells of tight gas, it is necessary to develop an environmentally-friendly treatment agent with a strong ability to inhibit pulping and at the same time take into account wellbore stability and friction torque, so as to solve the problems existing in the water-based drilling fluid of tight gas.

SUMMARY

The present disclosure is to provide a quaternary ammonium salt and a preparation method and use thereof as an inhibitor, and a water-based drilling fluid and use thereof. The quaternary ammonium salt provided by the present disclosure is environmentally-friendly. The quaternary ammonium salt could be used as an inhibitor for water-based drilling fluids, has good inhibition performance, as well as wellbore stabilization, and lubricating performance, and is suitable for tight gas production.

To achieve the above object of the present disclosure, the present disclosure provides the following technical solutions:

The present disclosure provides a quaternary ammonium salt, having a structure shown in formula I.

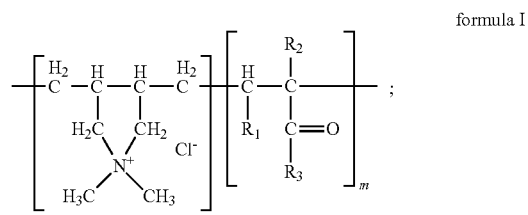

formula I wherein, in the formula I, $R_1$ is selected from the group consisting of —H and —COOH;

$R_2$ is selected from the group consisting of —H and —CH$_2$—COOH;

$R_3$ is selected from the group consisting of —NH—CH$_2$—CH$_2$—CH$_2$—NH$_2$, —NH—CH$_2$—CH$_2$—NH$_2$, —NH—CH$_2$—CH$_2$—OH, —O—CH$_2$—CH$_2$—NH$_2$, —N—(CH$_2$—CH$_2$—OH)$_2$, and —O—CH$_2$—CH$_2$—NH—CH$_2$—CH$_2$—OH; and n and m are independently 10 to 15.

In some embodiments, in the formula I, $R_1$ is —H, $R_2$ is —CH$_2$—COOH, $R_3$ is —NH—CH$_2$—CH$_2$—NH$_2$, and n and m are independently 12 to 15; or in the formula I, $R_1$ is —COOH, $R_2$ is —H, $R_3$ is —NH—CH$_2$—CH$_2$—OH, and n and m are independently 10 to 12; or in the formula I, $R_1$ is —H, $R_2$ is —H, $R_3$ is selected from the group consisting of —NH—CH$_2$—CH$_2$—NH$_2$ and —N—(CH$_2$—CH$_2$—OH)$_2$, n is 10 to 12 and m is 12 to 15.

The present disclosure further provides a method for preparing the quaternary ammonium salt as described in the above technical solutions, comprising:

mixing dimethyl diallyl ammonium chloride, a double bond-containing organic acid, an initiator and water to obtain a first mixture, and conducting free radical aqueous solution polymerization reaction on the first mixture to obtain a copolymer system; and mixing the copolymer system, a water-soluble organic amine and a catalyst to obtain a second mixture, and conducting condensation reaction on the second mixture to obtain the quaternary ammonium salt having a structure shown in the formula I, wherein the double bond-containing organic acid is one or more selected from the group consisting of itaconic acid, acrylic acid, and maleic acid; and the water-soluble organic amine is one or more selected from the group consisting of ethylenediamine, 1,2-diaminopropane, monoethanolamine, and diethanolamine.

In some embodiments, a mass ratio of DMDAAC, the double bond-containing organic acid, the water-soluble organic amine, and water is in a range of (10-15): (10-15): (10-20):(70-80).

In some embodiments, the free radical aqueous solution polymerization reaction is conducted at a temperature of 60° C. to 70° C. for 5 h to 7 h.

In some embodiments, the condensation reaction is conducted at a temperature of 150° C. to 170° C. for 5 h to 7 h.

The present disclosure further provides use of the quaternary ammonium salt as described in the above technical solutions or the quaternary ammonium salt prepared by the method as described in the above technical solutions as an inhibitor.

The present disclosure further provides a water-based drilling fluid, comprising water, a pH regulator, a rheology modifier, a polymer viscosifying and filtration additive, a filtrate reducer, an inhibitor, and a weighting agent, wherein the inhibitor is the quaternary ammonium salt as described in the above technical solutions or the quaternary ammonium salt prepared by the preparation method as described in the above technical solutions.

In some embodiments, based on a mass of water, the pH regulator is in an amount of 0.5 to 1.5% by mass, the rheology modifier is in an amount of 0.3 to 0.5% by mass, the polymer viscosifying and filtration additive is in an amount of 0.5 to 1.5% by mass, the filtrate reducer is in an amount of 2.0 to 4.0% by mass, the inhibitor is in an amount of 15.0 to 35.0%, and the weighting agent is in an amount of 45.0 to 60.0% by mass.

The present disclosure further provides use of the water-based drilling fluid as described in the above technical solutions for tight gas exploitation.

The present disclosure provides a quaternary ammonium salt. The quaternary ammonium salt provided by the present disclosure is environmentally-friendly. The quaternary ammonium salt could be used as an inhibitor for water-based drilling fluids, has excellent inhibitory performance, as well as desirable lubricating performance, plugging performance, and stability, and is suitable for tight gas exploitation.

The present disclosure provides a method for preparing the quaternary ammonium salt. In the present disclosure, DMDAAC, a double bond-containing organic acid, and a water-soluble organic amine are used as raw materials, water is used as a solvent, and the raw materials are all environmentally-friendly. The prepared quaternary ammonium salt is a multifunctional and environmentally-friendly inhibitor, having desirable compatibility with the environment. In addition, the method for preparing the quaternary ammonium salt provided by the present disclosure has simple operations.

DETAILED DESCRIPTION OF THE EMBODIMENTS

The present disclosure provides a quaternary ammonium salt, having a structure shown in formula I.

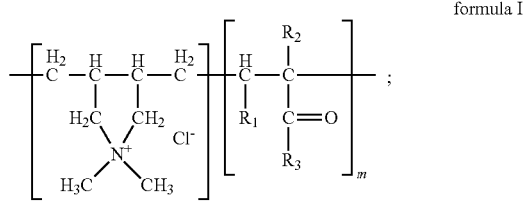

formula I wherein, in the formula I, $R_1$ is selected from the group consisting of —H and —COOH;

$R_2$ is selected from the group consisting of —H and —CH$_2$—COOH;

$R_3$ is selected from the group consisting of —NH—CH$_2$—CH$_2$—CH$_2$—NH$_2$, —NH—CH$_2$—CH$_2$—NH$_2$, —NH—CH$_2$—CH$_2$—OH, —O—CH$_2$—CH$_2$—NH$_2$, —N—(CH$_2$—CH$_2$—OH)$_2$, and —O—CH$_2$—CH$_2$—NH—CH$_2$—CH$_2$—OH; and n and m are independently 10 to 15.

In the present disclosure, n and m are independently 10 to 15; specifically, in some embodiments, n and m are independently 10 to 12 or 12 to 15.

In the examples of the present disclosure, in the formula I, $R_1$ is —H, $R_2$ is —CH$_2$—COOH, $R_3$ is —NH—CH$_2$—CH$_2$—NH$_2$, and n and m are independently 12 to 15; or in the formula I, $R_1$ is —COOH, $R_2$ is —H, $R_3$ is —NH—CH$_2$—CH$_2$—OH, and n and m are independently 10 to 12; or in the formula I, $R_1$ is —H, $R_2$ is —H, $R_3$ is selected from the group consisting of —NH—CH$_2$—CH$_2$—NH$_2$ and —N—(CH$_2$—CH$_2$—OH)$_2$, n is 10 to 12, and m is 12 to 15.

The quaternary ammonium salt provided by the present disclosure contains a large number of adsorption groups, such as amine groups and amide groups, which lead to the formation of multiple adsorption sites on the surface of mudstone, while the side chain contains more cations. The amino group of the quaternary ammonium salt in an aqueous solution is positively charged. The quaternary ammonium salt contains a large number of quaternary ammonium groups. Therefore, the quaternary ammonium salt can be strongly adsorbed on the surface of the mudstone through electrostatic interaction, so that the absolute value of the negative charge on the surface of clay particles is reduced, thus weakening electrostatic repulsion and repulsion of the surface hydration film on the surface of the mudstone. The synergistic effect of the two will bind the mudstone tightly, preventing its hydration, dispersion and expansion. In addition, due to the fact that the quaternary ammonium salt provided by the present disclosure contains a large number of adsorption groups, it can form a dense oil film on the metal surface and rock well wall. As an inhibitor for water-based drilling fluids, the quaternary ammonium salt can improve the lubricity of the water-based drilling fluids, and can form a spatial network structure after being dispersed in the water-based drilling fluids. The structure is filled with solid phase particles in the water-based drilling fluids (specifically, refers to the weighting agent, filtrate reducer, and polymer viscosifying and filtration additive), thus being beneficial to improving the plugging performance of the water-based drilling fluids.

The present disclosure further provides a method for preparing the quaternary ammonium salt as described in the above technical solutions, comprising:

mixing dimethyl diallyl ammonium chloride (DMDAAC), a double bond-containing organic acid, an initiator and water to obtain a first mixture, and conducting free radical aqueous solution polymerization reaction on the first mixture to obtain a copolymer system; and mixing the copolymer system, a water-soluble organic amine and a catalyst to obtain a second mixture, and conducting condensation reaction on the second mixture to obtain the quaternary ammonium salt having a structure shown in the formula I, wherein the double bond-containing organic acid is one or more selected from the group consisting of itaconic acid, acrylic acid, and maleic acid; and the water-soluble organic amine is one or more selected from the group consisting of ethylenediamine, 1,2-diaminopropane, monoethanolamine, and diethanolamine.

In the present disclosure, dimethyl diallyl ammonium chloride (DMDAAC), a double bond-containing organic acid, an initiator and water are mixed to obtain a first mixture, and conducted free radical aqueous solution polymerization reaction on the first mixture to obtain a copolymer system. In the present disclosure, the double bond-containing organic acid is one or more selected from the group consisting of itaconic acid, acrylic acid, and maleic acid, preferably itaconic acid, acrylic acid, or an itaconic acid-maleic acid mixture. In some embodiments, in the itaconic acid-maleic acid mixture, a mass ratio of itaconic acid to maleic acid is in a range of (4-8): (2-6), preferably 6:4. In the present disclosure, in some embodiments, a mass ratio of DMDAAC to the double bond-containing organic acid is in a range of (10-15): (10-15), specifically 1:1 or 1:1.5. In the present disclosure, in some embodiments, the initiator is selected from the group consisting of benzoyl peroxide, 2,2'-azobis[2-methylpropionamidine]dihydrochloride (AIBA), and a $(NH_4)_2S_2O_8$—$NaHSO_3$ mixture; in some embodiments, in the $(NH_4)_2S_2O_8$—$NaHSO_3$ mixture, a mass ratio of $(NH_4)_2S_2O_8$ to $NaHSO_3$ is in a range of (0.5-2): (1-3), preferably 1:2. In some embodiments, a mass ratio of the initiator to DMDAAC is in a range of (0.5-1): (10-15), specifically 0.5:10, 0.8:10, or 1:15. In the present disclosure, in some embodiments, a mass ratio of water to DMDAAC is in a range of (70-80): (10-15), specifically 70:15, 75:10, or 80:10.

In the present disclosure, in some embodiments, a method for mixing DMDAAC, the double bond-containing organic acid, the initiator and water comprises: mixing water, DMDAAC and the double bond-containing organic acid, heating a resulting mixture under stirring to a temperature required for the free radical aqueous solution polymerization reaction, and then adding the initiator in a protective atmosphere. In the present disclosure, there is no special limitation on the type of protective gas providing the protective atmosphere, and the protective gas well known to those skilled in the art may be used, such as nitrogen. In the present disclosure, the free radical aqueous solution polymerization reaction is conducted at a temperature of 60° C. to 70° C., specifically 60° C., 65° C., or 70° C. In some embodiments, the free radical aqueous solution polymerization reaction is conducted for 5 h to 7 h, specifically 5 h, 6 h, or 7 h; and the free radical aqueous solution polymerization reaction is conducted in a protective atmosphere. In some embodiments, the free radical aqueous solution polymerization reaction is conducted in a Parr4566 type reactor.

In the present disclosure, the free radical aqueous solution polymerization reaction does not need any post-treatment. The resulting graft polymer, a water-soluble organic amine and a catalyst are directly mixed to obtain a second mixture, and conducted condensation reaction on the second mixture to obtain the quaternary ammonium salt having a structure shown in the formula I. In the present disclosure, the water-soluble organic amine is one or more selected from the group consisting of ethylenediamine, 1,2-diaminopropane, monoethanolamine, and diethanolamine, preferably ethylenediamine, monoethanolamine, and an ethylenediamine-diethanolamine mixture. In some embodiments, in the ethylenediamine-diethanolamine mixture, a mass ratio of ethylenediamine to diethanolamine is in a range of (0.5-2):1, preferably 1:1. In the present disclosure, in some embodiments, a mass ratio of the water-soluble organic amine to DMDAAC is in a range of (10-20):(10-15), preferably 10:15, 15:10, or 20:10. In the present disclosure, in some embodiments, the catalyst is selected from the group consisting of sodium methoxide, KOH, and NaOH, preferably sodium methoxide. In some embodiments, a mass ratio of the catalyst to DMDAAC is in a range of (1-2): (10-15), specifically 1:10 or 2:10.

In the present disclosure, in some embodiments, the condensation reaction is conducted at a temperature of 150° C. to 170° C., specifically 150° C., 160° C., or 170° C. In some embodiments, the condensation reaction is conducted for 5 h to 7 h, specifically 5 h, 6 h, or 7 h. In some embodiments, the condensation reaction is conducted under stirring. In the present disclosure, the condensation reaction does not require any post-treatment. The resulting product system containing the quaternary ammonium salt could be directly used as an inhibitor.

The present disclosure further provides use of the quaternary ammonium salt as described in the above technical solutions or the quaternary ammonium salt prepared by the method as described in the above technical solutions as an inhibitor.

The present disclosure provides a water-based drilling fluid, comprising water, a pH regulator, a rheology modifier, a polymer viscosifying and filtration additive, a filtrate reducer, an inhibitor, and a weighting agent, wherein the inhibitor is the quaternary ammonium salt as described in the above technical solutions or the quaternary ammonium salt prepared by the method as described in the above technical solutions. In the present disclosure, in some embodiments, based on a mass of water, the pH regulator is in an amount of 0.5 to 1.5% by mass, the rheology modifier is in an amount of 0.3 to 0.5% by mass, the polymer viscosifying and filtration additive is in an amount of 0.5 to 1.5% by mass, the filtrate reducer is in an amount of 2.0 to 4.0% by mass, the inhibitor is in an amount of 15.0 to 35.0%, and the weighting agent is in an amount of 45.0 to 60.0% by mass. The above components will be specifically described below.

In the present disclosure, in some embodiments, the water is freshwater or seawater.

In the present disclosure, in some embodiments, the pH regulator accounts for 0.5 to 1.5% of the mass of water, specifically 0.5%, 1.0%, or 1.5%. In the present disclosure, in some embodiments, the pH regulator is one or two selected from the group consisting of sodium hydroxide and light magnesium oxide, preferably a sodium hydroxide-light magnesium oxide mixture. In some embodiments, in the sodium hydroxide-light magnesium oxide mixture, a mass ratio of sodium hydroxide to light magnesium oxide is in a range of (3-6): (4-7), specifically 3:7, 4:6, 5:5, or 6:4. In the present disclosure, sodium hydroxide can provide an alkaline environment for water-based drilling fluids, which is beneficial for polymers (specifically, refers to the quaternary ammonium salt and the filtrate reducer, the rheology modifier, and the polymer viscosifying and filtration additive) to form a stable grid structure in aqueous solutions. Light magnesium oxide has a strong buffer capacity, which can keep the pH value of the water-based drilling fluid stable, and inhibit the chain-breaking and decomposition of the grid structure formed by the polymer. In the present disclosure, in some embodiments, the amount of the pH regulator is limited to the above range, and the resulting water-based drilling fluid has a pH value of 9 to 11, specifically 9, 10, or 11.

In the present disclosure, in some embodiments, the rheology modifier accounts for 0.3 to 0.5% of the mass of water, specifically 0.3%, 0.4%, or 0.5%. In some embodiments, the rheology modifier is one or more selected from the group consisting of xanthan gum, Welan gum, and tamarind gum, preferably a xanthan gum-Welan gum-tamarind gum mixture; in some embodiments, in the xanthan gum-Welan gum-tamarind gum mixture, a mass ratio of xanthan gum, Welan gum, and tamarind gum is in a range of (6-8): (1-2):(1-2), specifically 6:2:2, 6.5:1.5:2, 7:1.5:1.5, or 8:1:1. In the present disclosure, Welan gum has desirable temperature stability, and can play a synergistic effect after compounding with xanthan gum and tamarind gum, thereby further ensuring that the rheology modifier has excellent temperature resistance.

In the present disclosure, in some embodiments, the polymer viscosifying and filtration additive accounts for 0.5 to 1.5% of the mass of water, specifically 0.5%, 1.0%, or 1.5%. In some embodiments, the polymer viscosifying and filtration additive is polyacrylamide, and polyacrylamide has a relative molecular mass of 0.8 million to 1 million. In the present disclosure, in some embodiments, polyacrylamide is used as the polymer viscosifying and filtration additive; polyacrylamide has desirable temperature and salt resistance and desirable compatibility with other treatment agents.

In the present disclosure, in some embodiments, the filtrate reducer accounts for 2.0 to 4.0% of the mass of water, specifically 2.0%, 3.0%, or 4.0%. In some embodiments, the filtrate reducer is one or more selected from the group consisting of sodium carboxymethylcellulose, hydroxypropyl starch (HPS), and carboxymethyl starch, preferably a sodium carboxymethylcellulose-hydroxypropyl starch-carboxymethyl starch mixture; in the sodium carboxymethylcellulose-hydroxypropyl starch-carboxymethyl starch mixture, a mass ratio of sodium carboxymethylcellulose, hydroxypropyl starch, and carboxymethyl starch is in a range of (3-5): (2-4):(3-5), specifically 3:3:4, 4:4:2, 5:2:3, or 3:2:5. In the present disclosure, in some embodiments, the filtrate reducer with the above compositions is used, wherein sodium carboxymethylcellulose, hydroxypropyl starch, and carboxymethyl starch have a synergistic effect, which can better reduce filtrate and reduce the permeability of mud cake; meanwhile, all above three belong to modified plant polymers and are environmentally-friendly.

In the present disclosure, in some embodiments, the inhibitor accounts for 15.0 to 35.0% of the mass of water, specifically 15.0%, 20.0%, 25.0%, or 35.0%. The quaternary ammonium salt provided by the present disclosure is used as an inhibitor for water-based drilling fluids, has desirable inhibition performance, as well as desirable lubricating performance, plugging performance, and stability, is suitable for tight gas exploitation, and is environmentally-friendly.

In the present disclosure, in some embodiments, the weighting agent accounts for 45.0 to 60.0% of the mass of water. In the present disclosure, in some embodiments, the weighting agent is barite. In the present disclosure, in some embodiments, the amount of the weighting agent is limited to the above range, and the resulting water-based drilling fluid has a density of 1.3 g/cm$^3$ to 1.4 g/cm$^3$.

The present disclosure provides use of the water-based drilling fluid as described in the above technical solutions for tight gas exploitation.

The technical solutions of the present disclosure will be clearly and completely described below with reference to the examples of the present disclosure. It is obvious that the described examples are only part of the examples of the present disclosure, not all of them. All other examples made by those of ordinary skill in the art based on the examples of the present disclosure without creative efforts should fall within the protection scope of the present disclosure.

Example 1

In parts by mass, 70 parts of water, 15 parts of dimethyl diallyl ammonium chloride (DMDAAC), and 15 parts of itaconic acid were added into a Parr4566 type reactor and heated to 60° C. under stirring. After introducing nitrogen for 30 min, 1 part of initiator benzoyl peroxide was added thereto, stirred at a constant temperature and subjected to a reaction for 6 h. Then 10 parts of ethylenediamine and 1.5 parts of catalyst sodium methoxide were added into the reactor, obtaining a reactant. The reactor was sealed. The resulting reactant was heated to 150° C. under stirring, stirred at a constant temperature and subjected to a reaction for 7 h, obtaining an inhibitor (denoted as YZ-1; wherein $R_1$ was —H, $R_2$ was —CH$_2$—COOH, $R_3$ was —NH—CH$_2$—CH$_2$—NH$_2$, and n and m each were 12 to 15).

In order to conduct subsequent performance tests to evaluate the inhibition performance of the inhibitor in freshwater, in parts by mass, 80 parts of freshwater and 20 parts of the inhibitor (YZ-1) were mixed, obtaining a water-based drilling fluid.

Example 2

In parts by mass, 80 parts of water, 10 parts of dimethyl diallyl ammonium chloride (DMDAAC), and 10 parts of a double bond-containing organic acid (specifically itaconic acid and maleic acid, wherein a mass ratio of itaconic acid to maleic acid was 6:4) were added into a Parr4566 type reactor and heated to 65° C. under stirring. After introducing nitrogen for 30 min, 0.5 parts of initiator benzoyl peroxide was added thereto, stirred at a constant temperature and subjected to a reaction for 5 h. Then 15 parts of monoethanolamine and 1.0 part of catalyst sodium methoxide were added into the reactor, obtaining a reactant. The reactor was sealed. The resulting reactant was heated to 160° C. under stirring, stirred at a constant temperature and subjected to a reaction for 5 h, obtaining an inhibitor (denoted as YZ-2; wherein $R_1$ was —COOH, $R_2$ was —H, $R_3$ was —NH—CH$_2$—CH$_2$—OH, and n and m each were 10 to 12).

In order to conduct subsequent performance tests to evaluate the inhibition performance of the inhibitor in freshwater, in parts by mass, 85 parts of freshwater and 15 parts of the inhibitor (YZ-2) were mixed, obtaining a water-based drilling fluid.

Example 3

In parts by mass, 75 parts of water, 10 parts of dimethyl diallyl ammonium chloride (DMDAAC), and 15 parts of acrylic acid were added into a Parr4566 type reactor and heated to 70° C. under stirring. After introducing nitrogen for 30 min, 0.8 parts of initiator benzoyl peroxide was added thereto, stirred at a constant temperature and subjected to a reaction for 7 h. Then 20 parts of a water-soluble organic amine (specifically ethylenediamine and diethanolamine, wherein a mass ratio of ethylenediamine to diethanolamine was 1:1) and 2.0 parts of catalyst sodium methoxide were added into the reactor, obtaining a reactant. The reactor was sealed. The resulting reactant was heated to 170° C. under stirring, stirred at a constant temperature and subjected to a reaction for 6 h, obtaining an inhibitor (denoted as YZ-3; wherein $R_1$ was —H, $R_2$ was —H, $R_3$ was selected from the group consisting of —NH—CH$_2$—CH$_2$—NH$_2$ (corresponding to ethylenediamine) and —N—(CH$_2$—CH$_2$—OH)$_2$ (corresponding to diethanolamine), and n was 10 to 12 and m was 12 to 15).

In order to conduct subsequent performance tests to evaluate the inhibition performance of the inhibitor in freshwater, in parts by mass, 75 parts of freshwater and 25 parts of the inhibitor (YZ-3) were mixed, obtaining a water-based drilling fluid.

Example 4

In this example, the water-based drilling fluid consisted of water, a pH regulator, a rheology modifier, a polymer viscosifying and filtration additive, a filtrate reducer, an inhibitor, and a weighting agent.

Based on the mass of water, an amount of the pH regulator was 1.0% by mass, an amount the rheology modifier was 0.5% by mass, an amount of the polymer viscosifying and filtration additive was 1.0% by mass, an amount of the filtrate reducer was 3.0% by mass, an amount of the inhibitor was 15.0% by mass, and an amount of the weighting agent was 45.0% by mass.

Wherein, the water was freshwater; the pH regulator was sodium hydroxide and light magnesium oxide, and a mass ratio of sodium hydroxide to light magnesium oxide was 3:7; the rheology modifier was xanthan gum, Welan gum, and tamarind gum, and a mass ratio of xanthan gum, Welan gum, and tamarind gum was 6:2:2; the polymer viscosifying and filtration additive was polyacrylamide with a relative molecular mass of 0.8 million to 1 million; the filtrate reducer was sodium carboxymethylcellulose, hydroxypropyl starch (HPS), and carboxymethyl starch, and a mass ratio of sodium carboxymethylcellulose, hydroxypropyl starch, and carboxymethyl starch was 3:3:4; the inhibitor was the YZ-1 prepared in Example 1; and the weighting agent was barite (a commercially-available commodity).

The water-based drilling fluid had a density of 1.3 g/cm$^3$ and a pH value of 10.

Example 5

In this example, the water-based drilling fluid consisted of water, a pH regulator, a rheology modifier, a polymer viscosifying and filtration additive, a filtrate reducer, an inhibitor, and a weighting agent.

Based on the mass of water, an amount of the pH regulator was 0.5% by mass, an amount the rheology modifier was 0.4% by mass, an amount of the polymer viscosifying and filtration additive was 1.0% by mass, an amount of the filtrate reducer was 4.0% by mass, an amount of the inhibitor was 20.0% by mass, and an amount of the weighting agent was 60.0% by mass.

Wherein, the water was seawater; the pH regulator was sodium hydroxide and light magnesium oxide, and a mass ratio of sodium hydroxide to light magnesium oxide was 6:4; the rheology modifier was xanthan gum, Welan gum, and tamarind gum, and a mass ratio of xanthan gum, Welan gum, and tamarind gum was 8:1:1; the polymer viscosifying and filtration additive was polyacrylamide with a relative molecular mass of 0.8 million to 1 million; the filtrate reducer was sodium carboxymethylcellulose, hydroxypropyl starch (HPS), and carboxymethyl starch, and a mass ratio of sodium carboxymethylcellulose, hydroxypropyl starch, and carboxymethyl starch was 4:4:2; the inhibitor was the YZ-2 prepared in Example 2; and the weighting agent was barite (a commercially-available commodity).

The water-based drilling fluid had a density of 1.4 g/cm$^3$ and a pH value of 9.

Example 6

In this example, the water-based drilling fluid consisted of water, a pH regulator, a rheology modifier, a polymer viscosifying and filtration additive, a filtrate reducer, an inhibitor, and a weighting agent.

Based on the mass of water, an amount of the pH regulator was 1.0% by mass, an amount the rheology modifier was 0.4% by mass, an amount of the polymer viscosifying and filtration additive was 0.5% by mass, an amount of the filtrate reducer was 2.0% by mass, an amount of the inhibitor was 25.0% by mass, and an amount of the weighting agent was 45.0% by mass.

Wherein, the water was freshwater; the pH regulator was sodium hydroxide and light magnesium oxide, and a mass ratio of sodium hydroxide to light magnesium oxide was 50:50; the rheology modifier was xanthan gum, Welan gum, and tamarind gum, and a mass ratio of xanthan gum, Welan gum, and tamarind gum was 7:1.5:1.5; the polymer viscosifying and filtration additive was polyacrylamide with a relative molecular mass of 0.8 million to 1 million; the filtrate reducer was sodium carboxymethylcellulose, hydroxypropyl starch (HPS), and carboxymethyl starch, and a mass ratio of sodium carboxymethylcellulose, hydroxypropyl starch, and carboxymethyl starch was 5:2:3; the inhibitor was the YZ-3 prepared in Example 3; and the weighting agent was barite (a commercially-available commodity).

The water-based drilling fluid had a density of 1.3 g/cm$^3$ and a pH value of 10.

Example 7

In this example, the water-based drilling fluid consisted of water, a pH regulator, a rheology modifier, a polymer viscosifying and filtration additive, a filtrate reducer, an inhibitor, and a weighting agent.

Based on the mass of water, an amount of the pH regulator was 1.5% by mass, an amount the rheology modifier was 0.3% by mass, an amount of the polymer viscosifying and filtration additive was 1.5% by mass, an amount of the filtrate reducer was 2.0% by mass, an amount of the inhibitor was 35.0% by mass, and an amount of the weighting agent was 60.0% by mass.

Wherein, the water was seawater; the pH regulator was sodium hydroxide and light magnesium oxide, and a mass ratio of sodium hydroxide to light magnesium oxide was 4:6; the rheology modifier was xanthan gum, Welan gum, and tamarind gum, and a mass ratio of xanthan gum, Welan gum, and tamarind gum was 6.5:1.5:2; the polymer viscosifying and filtration additive was polyacrylamide with a relative molecular mass of 0.8 million to 1 million; the filtrate reducer was sodium carboxymethylcellulose, hydroxypropyl starch (HPS), and carboxymethyl starch, and a mass ratio of sodium carboxymethylcellulose, hydroxypropyl starch, and carboxymethyl starch was 3:2:5; the inhibitor was the YZ-3 prepared in Example 3; and the weighting agent was barite (a commercially-available commodity).

The water-based drilling fluid had a density of 1.4 g/cm$^3$ and a pH value of 11.

Comparative Example 1

100 parts by mass of freshwater was used.

Comparative Example 2

100 parts by mass of white oil was used.

Comparative Example 3

95 parts by mass of freshwater and 5 parts by mass of polyamine inhibitor (with a weight average molecular weight of 300 to 600) were fully mixed, obtaining a mixed solution.

Comparative Example 4

In parts by mass, 100 parts of seawater, 0.2 parts of NaOH, 0.25 parts of $Na_2CO_3$, 1.0 part of polyacrylamide, 0.3 parts of Welan gum (as a rheology modifier), 2.0 parts of sodium carboxymethylcellulose, 2.0 parts of carboxymethyl starch, 7.0 parts of KCl, 2.0 parts of a polyamine inhibitor, 2.0 parts of fatty alcohol poly oxypropylene ether (as a lubricant), 3.0 parts of sulfonated bitumen (as a plugging agent), and barite were mixed, obtaining a water-based drilling fluid with a density of 1.4 $g/cm^3$.

Comparative Example 5

In parts by mass, 85 parts of white oil, 15 parts of a saturated calcium chloride aqueous solution, 2.5 parts of organic soil, 4.0 parts of a main emulsifier, 1.0 part of an auxiliary emulsifier, 0.5 parts of a shear strength improving agent, 2.0 parts of an alkalinity modifier, 2.5 parts of a filtrate reducer, 2.5 parts of a plugging agent, and 100 parts of barite were mixed, obtaining an oil-based drilling fluid with a density of 1.4 $g/cm^3$.

Test Example 1

The biotoxicity of inhibitors was tested according to GB/T 18420.2-2009 (Test method for biological toxicity for pollutants from marine petroleum exploration and exploitation). The degradation performance of inhibitors was analyzed according to SY/T 6788-2020 (Evaluation procedures of environmental protection for water-soluble oilfield chemicals). The specific results are shown in Table 1.

TABLE 1

Evaluation results of the environmental performance of inhibitors

| Inhibitor | $LC_{50}$ (mg/L) | $BOD_5/COD_{Cr}$ (%) |
|---|---|---|
| YZ-1 | 67219 | 28.1 |
| YZ-2 | 57820 | 26.5 |
| YZ-3 | 62170 | 26.2 |

Notes: The amounts of the inhibitors were 20%; LC50 refers to the half-death concentration of Artemia (mg/L); $COD_{cr}$ refers to chemical oxygen demand (mg/L); $BOD_5$ refers to biochemical oxygen demand (mg/L).

It can be seen from Table 1 that the inhibitors have LC50 of greater than 30,000 mg/L and $BOD_5/COD_{cr}$ values of greater than 25%, which indicates that the inhibitors are environmentally-friendly.

Test Example 2

The inhibitory performance of the drilling fluids in Examples 1 to 7 and Comparative Examples 1 to 4 was evaluated, respectively. Specifically: dried outcrop soil was crushed into 6 to 10 mesh particles; 350 mL of the drilling fluid was added to an aging tank; 50 g of the outcrop soil was added thereto; then the aging tank was placed in a roller furnace and rolled at 120° C. for 16 h, obtaining a mixture; after cooling, the resulting mixture was poured, and passed through a 40-mesh sieve; a part of the resulting particles on the sieve was taken, dried at 105° C. for 4 h, and weighed. Based on this, a rolling recovery rate was calculated.

TABLE 2

Test results of the inhibition performance of drilling fluids

| Drilling fluid source | G |
|---|---|
| Example 1 | 88.9 |
| Example 2 | 90.8 |
| Example 3 | 92.5 |
| Example 4 | 91.5 |
| Example 5 | 94.6 |
| Example 6 | 97.3 |
| Example 7 | 99.2 |
| Comparative Example 1 | 3.2 |
| Comparative Example 2 | 90.2 |
| Comparative Example 3 | 41.9 |
| Comparative Example 4 | 85.8 |
| Comparative Example 5 | 94.1 |

Notes: The condition of the hot rolling was 120° C.×16 h; G refers to the rolling recovery rate of the outcrop soil in drilling fluids (%).

It can be seen from Table 2 that the outcrop soil in freshwater has a rolling recovery rate of only 3.2%. The content of the inhibitors prepared in the examples according to the present disclosure in the aqueous solution increases, and the rolling recovery rate of the outcrop soil increases gradually, which significantly improves the rolling recovery rate of the outcrop soil, and is higher than the rolling recovery rate of outcrop soil in white oil and polyamine-containing inhibitor solutions, showing excellent inhibition performance. In addition, the inhibitors prepared in the examples according to the present disclosure are used in the water-based drilling fluid, and can make the rolling recovery rate of outcrop soil greater than 9000. The inhibition performance of the inhibitor is similar to that of oil-based drilling fluid.

Test Example 3

According to the standard GB/T16783.1-2014 (Petroleum and natural gas industries Field testing of drilling fluids-Part 1: Water-based fluids), the rheological and plugging performance of the drilling fluids in Examples 4 to 7 and Comparative Examples 4 to 5 after hot rolling were evaluated. The specific results are shown in Table 3.

TABLE 3

Evaluation results of the performance test of drilling fluids

| Drilling fluid source | PV | YP | Φ3 | PPT | M |
|---|---|---|---|---|---|
| Example 4 | 25 | 11 | 11 | 5.8 | 0.11 |
| Example 5 | 28 | 12 | 11 | 5.0 | 0.09 |
| Example 6 | 34 | 13 | 12 | 3.8 | 0.08 |
| Example 7 | 38 | 14 | 13 | 2.2 | 0.07 |
| Comparative Example 4 | 30 | 10 | 9 | 6.2 | 0.15 |
| Comparative Example 5 | 30 | 7 | 8 | 5.2 | 0.10 |

Notes: PV refers to the plastic viscosity of drilling fluids (mPa·s); YP refers to the dynamic shear force of drilling fluids (Pa); Φ3 refers to the 3-turn reading of a six-speed rotary viscometer (dimensionless); PPT refers to plugging filtrate (mL), specifically refers to the water loss volume under the conditions of 3.5 MPa, 120° C., and 30 min, using a sand table instead of filter paper; M refers to the friction coefficient of drilling fluids (dimensionless).

It can be seen from Table 3 that in the water-based drilling fluids provided by the present disclosure, as the content of the inhibitors increases, the filtrate of the water-based drilling fluids and the friction coefficient of the drilling fluids gradually decreases, indicating that the inhibitors have a certain improvement effect on the lubricating and plugging performances of the water-based drilling fluids, and are suitable for tight gas exploitation.

The above descriptions are merely the preferred embodiments of the present disclosure. It should be understood that for those skilled in the art, several improvements and modifications could be further made without departing from the principle of the present disclosure, and these improvements and modifications should be deemed as falling within the protection scope of the present disclosure.

What is claimed is:

1. A quaternary ammonium salt, having a structure shown in formula I:

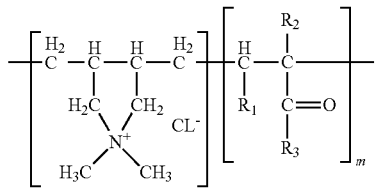

formula I;
wherein, in the formula I,
$R_1$ is selected from the group consisting of —H and —COOH;
$R_2$ is selected from the group consisting of —H and —CH$_2$—COOH;
$R_3$ is selected from the group consisting of —NH—CH$_2$—CH$_2$—CH$_2$—NH$_2$, —NH—CH$_2$—CH$_2$—NH$_2$, —NH—CH$_2$—CH$_2$—OH, —O—CH$_2$—CH$_2$—NH$_2$, —N—(CH$_2$—CH$_2$—OH)$_2$, and —O—CH$_2$—CH$_2$—NH—CH$_2$—CH$_2$—OH; and
n and m are independently 10 to 15.

2. The quaternary ammonium salt of claim 1, wherein in the formula I, $R_1$ is —H, $R_2$ is —CH$_2$—COOH, $R_3$ is —NH—CH$_2$—CH$_2$—NH$_2$, and n and m are independently 12 to 15; or
in the formula I, $R_1$ is —COOH, $R_2$ is —H, $R_3$ is —NH—CH$_2$—CH$_2$—OH, and n and m are independently 10 to 12; or
in the formula I, $R_1$ is —H, $R_2$ is —H, $R_3$ is selected from the group consisting of —NH—CH$_2$—CH$_2$—NH$_2$ and —N—(CH$_2$—CH$_2$—OH)$_2$, n is 10 to 12, and m is 12 to 15.

3. A method for preparing the quaternary ammonium salt of claim 1, comprising:
mixing dimethyl diallyl ammonium chloride, a double bond-containing organic acid, an initiator and water to obtain a first mixture, and conducting free radical aqueous solution polymerization reaction on the first mixture to obtain a copolymer system; and
mixing the copolymer system, a water-soluble organic amine and a catalyst to obtain a second mixture, and conducting condensation reaction on the second mixture to obtain the quaternary ammonium salt having a structure shown in the formula I,
wherein the double bond-containing organic acid is one or more selected from the group consisting of itaconic acid, acrylic acid, and maleic acid; and the water-soluble organic amine is one or more selected from the group consisting of ethylenediamine, 1,2-diaminopropane, monoethanolamine, and diethanolamine.

4. The method of claim 3, wherein a mass ratio of dimethyl diallyl ammonium chloride, the double bond-containing organic acid, the water-soluble organic amine, and water is in a range of (10-15): (10-15):(10-20):(70-80).

5. The method of claim 3, wherein the free radical aqueous solution polymerization reaction is conducted at a temperature of 60° C. to 70° C. for 5 h to 7 h.

6. The method of claim 3, wherein the condensation reaction is conducted at a temperature of 150° C. to 170° C. for 5 h to 7 h.

7. An inhibitor, comprising the quaternary ammonium salt of claim 1.

8. A water-based drilling fluid, comprising water, a pH regulator, a rheology modifier, a polymer viscosifying and filtration additive, a filtrate reducer, an inhibitor, and a weighting agent, wherein the inhibitor is the quaternary ammonium salt of claim 1.

9. The water-based drilling fluid of claim 8, wherein based on a mass of water, the pH regulator is in an amount of 0.5 to 1.5% by mass, the rheology modifier is in an amount of 0.3 to 0.5% by mass, the polymer viscosifying and filtration additive is in an amount of 0.5 to 1.5% by mass, the filtrate reducer is in an amount of 2.0 to 4.0% by mass, the inhibitor is in an amount of 15.0 to 35.0%, and the weighting agent is in an amount of 45.0 to 60.0% by mass.

10. A method for exploiting tight gas, comprising using the water-based drilling fluid of claim 8.

11. The method of claim 3, wherein in the formula I, $R_1$ is —H, $R_2$ is —CH$_2$—COOH, $R_3$ is —NH—CH$_2$—CH$_2$—NH$_2$, and n and m are independently 12 to 15; or
in the formula I, $R_1$ is —COOH, $R_2$ is —H, $R_3$ is —NH—CH$_2$—CH$_2$—OH, and n and m are independently 10 to 12; or
in the formula I, $R_1$ is —H, $R_2$ is —H, $R_3$ is selected from the group consisting of —NH—CH$_2$—CH$_2$—NH$_2$ and —N—(CH$_2$—CH$_2$—OH)$_2$, n is 10 to 12, and m is 12 to 15.

12. The inhibitor of claim 7, wherein in the formula I, $R_1$ is —H, $R_2$ is —CH$_2$—COOH, $R_3$ is —NH—CH$_2$—CH$_2$—NH$_2$, and n and m are independently 12 to 15; or
in the formula I, $R_1$ is —COOH, $R_2$ is —H, $R_3$ is —NH—CH$_2$—CH$_2$—OH, and n and m are independently 10 to 12; or
in the formula I, $R_1$ is —H, $R_2$ is —H, $R_3$ is selected from the group consisting of —NH—CH$_2$—CH$_2$—NH$_2$ and —N—(CH$_2$—CH$_2$—OH)$_2$, n is 10 to 12, and m is 12 to 15.

13. The water-based drilling fluid of claim 8, wherein in the formula I, $R_1$ is —H, $R_2$ is —CH$_2$—COOH, $R_3$ is —NH—CH$_2$—CH$_2$—NH$_2$, and n and m are independently 12 to 15; or
in the formula I, $R_1$ is —COOH, $R_2$ is —H, $R_3$ is —NH—CH$_2$—CH$_2$—OH, and n and m are independently 10 to 12; or in the formula I, $R_1$ is —H, $R_2$ is —H, $R_3$ is selected from the group consisting of —NH—$CH_2$—$CH_2$—$NH_2$ and —N—($CH_2$—$CH_2$—OH)$_2$, n is 10 to 12, and m is 12 to 15.

14. The method of claim 10, wherein based on a mass of water, the pH regulator is in an amount of 0.5 to 1.5% by mass, the rheology modifier is in an amount of 0.3 to 0.5% by mass, the polymer viscosifying and filtration additive is in an amount of 0.5 to 1.5% by mass, the filtrate reducer is in an amount of 2.0 to 4.0% by mass, the inhibitor is in an amount of 15.0 to 35.0%, and the weighting agent is in an amount of 45.0 to 60.0% by mass.

* * * * *